(12) United States Patent
Molnar et al.

(10) Patent No.: US 7,670,296 B2
(45) Date of Patent: Mar. 2, 2010

(54) MULTI-PURPOSE CONNECTOR FOR BLOOD PRESSURE MEASUREMENT EQUIPMENT

(75) Inventors: Brian M. Molnar, Skaneateles, NY (US); Raymond A. Lia, Auburn, NY (US); Thaddeus J. Wawro, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 11/636,823

(22) Filed: Dec. 11, 2006

(65) Prior Publication Data

US 2008/0139950 A1    Jun. 12, 2008

(51) Int. Cl.
*A61B 5/02* (2006.01)

(52) U.S. Cl. ..................................... 600/485

(58) Field of Classification Search ........... 600/499, 600/485; 606/203; D24/129; 285/239
See application file for complete search history.

(56) References Cited

U.S. PATENT DOCUMENTS

| | | | |
|---|---|---|---|
| 3,538,940 A * | 11/1970 | Graham | 137/271 |
| 5,937,885 A * | 8/1999 | Sampson | 137/1 |
| 6,346,084 B1 | 2/2002 | Schnell et al. | |
| 6,422,086 B1 | 7/2002 | Dromms et al. | |
| 6,453,941 B1 * | 9/2002 | Milhas et al. | 137/515 |
| 6,481,291 B1 | 11/2002 | Lia et al. | |
| 6,578,428 B1 | 6/2003 | Dromms et al. | |
| 6,615,666 B1 | 9/2003 | Lia et al. | |
| 6,682,547 B2 * | 1/2004 | McEwen et al. | 606/202 |
| 2003/0151256 A1 * | 8/2003 | Guala | 285/332 |
| 2004/0193119 A1 * | 9/2004 | Canaud et al. | 604/247 |
| 2006/0217618 A1 | 9/2006 | Lia et al. | |

OTHER PUBLICATIONS

International Search Report and Written Opinion, Mailed May 19, 2008, (8 pages).

* cited by examiner

*Primary Examiner*—Patricia C Mallari
(74) *Attorney, Agent, or Firm*—Roger P. Bonenfant

(57) ABSTRACT

A connector for blood pressure measurement systems is provided, wherein the connector enables interchangeable individual connection of a cuff to various gage housings, including those equipped with a male fitting or a female fitting, yet wherein the presence of the connector also desirably prevents inadvertent connection of a gage housing to certain other medical equipment.

15 Claims, 4 Drawing Sheets

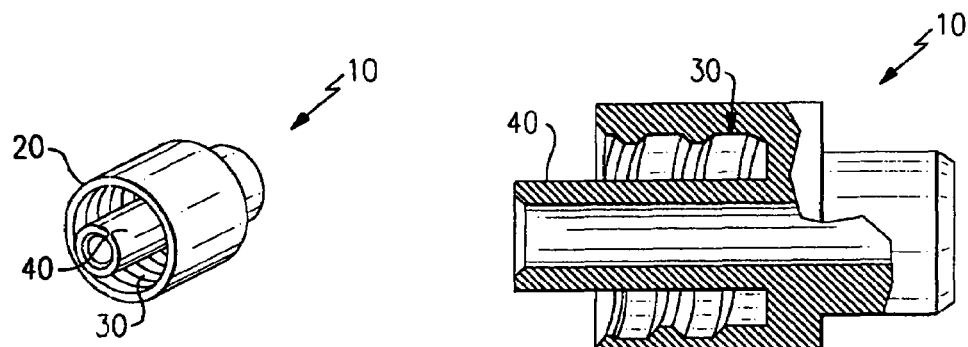
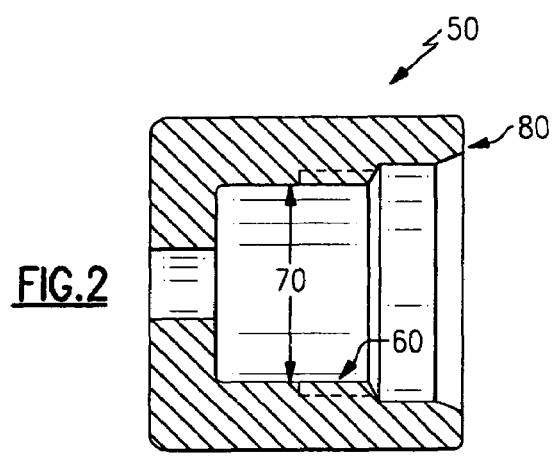
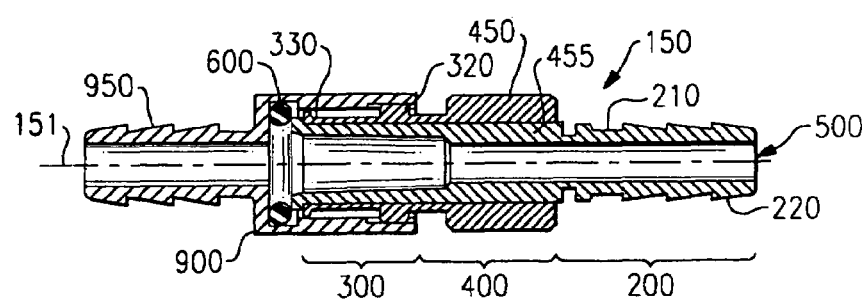

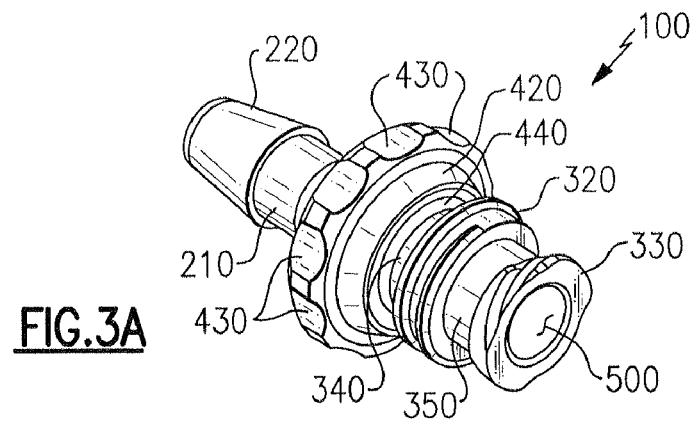
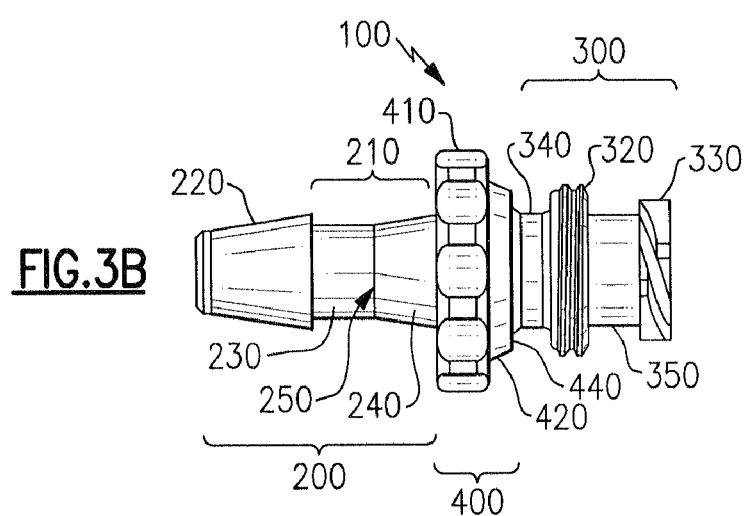
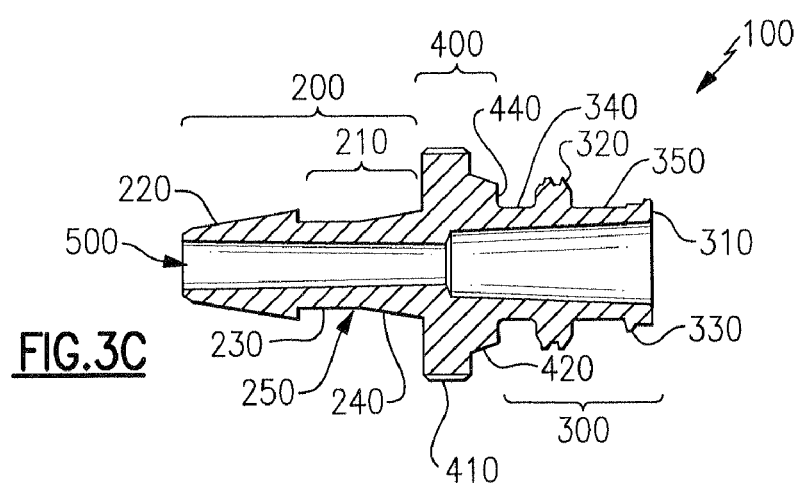

MULTI-PURPOSE CONNECTOR FOR BLOOD PRESSURE MEASUREMENT EQUIPMENT

FIELD OF THE INVENTION

The invention relates generally to the field of blood pressure measurement, and particularly to connectors that enable interchangeable connection of a blood pressure cuff to a wide variety of gage housings, yet that also prevent inadvertent connection of gage housings to certain other medical equipment.

BACKGROUND OF THE INVENTION

Sphygmomanometers are pressure measuring devices that are used to measure the arterial blood pressure of a patent. These devices typically include a pneumatic bulb, which inflates an interior pressure chamber of an attached cuff/sleeve that is fitted over a limb of the patient. A diaphragm or bellows assembly. responsive to changes in fluid pressure of the pneumatic bulb and the interior pressure chamber of the sleeve, is positioned in the housing of a gage (i.e., a gage housing), which is fluidly connected to the interior pressure chamber of the cuff.

The connection between the gage housing and the interior of the inflatable cuff generally occurs by connecting a section of elongated hose or tubing extending from the cuff to an inlet port that is disposed on one end of the gage housing. It is currently preferred to effect such a connection through use of a so-called "quick connect" arrangement. A quick connect arrangement is advantageous for several reasons, including the utilization of a minimum of connection parts, and because this form of connection enables a cuff to remain fitted over a limb of a patient, thus providing the patient with freedom of movement while still allowing for a blood pressure measurement to be taken, when necessary, by quickly connecting the cuff to a gage housing or other suitable apparatus.

A typical luer lock "quick-connect" fitting 10, as would extend from an inlet port of certain gage housings, is shown in FIGS. 1A and 1B. This fitting 10 includes an open connection end 20 having an internal luer thread 30 surrounding a cylindrical male connection element 40. The design of this type of fitting 10 (hereinafter referred to as a "male fitting") is advantageous in that it enables simple, yet reliable connection of the connection end 20 to a female luer lock (not shown), which is defined within or extending from a cuff.

Unfortunately, however, there are drawbacks directly related to the use of these types of male fittings 10. Most notably, because female luer locks are commonly utilized to connect various medical devices and equipment, their design can enable several different types of male fittings to be connected thereto, including those of unrelated devices and equipment. For example, based on its design, the female luer lock used to interconnect a patient's intravenous (IV) line to the male fitting at the end of IV drip can also be connected to the male fitting 10 shown in FIGS. 1A and 1B. This interconnection is problematic because if for some reason (e.g., untrained personnel, chaos) a connection were to occur between the male fitting 10 and the female luer lock of a patient's IV line, air could enter the patient's bloodstream and could potentially cause moderate to severe complications to the patient's health.

One solution to this design dilemma, as adopted in places such as Europe, has been to mandate that blood pressure measurement gages not be equipped with male fittings such as the FIGS. 1A and 1B fitting 10. Instead, it is common in these places to manufacture measurement gages that include a female fitting 50, such as shown in FIG. 2, in lieu of a male fitting. The female fitting 50 is designed to include internal threading 60 and an internal width 70, each of which are incompatible with female luer locks.

Thus, due to its design, incorporation of the female fitting 50 of FIG. 2 within blood pressure measurement systems beneficially prevents the occurrence of inadvertent—and potentially dangerous—connections between the male fitting 10 of FIG. 1 and the female luer lock provided on other medical devices and/or equipment (e.g., an IV line). At the same time, however, the incorporation of female luer locks to effect fluid connection between a cuff and a male fitting 10 disadvantageously renders thousands of existing cuffs that are still in circulation in the United States and worldwide obsolete. Consequently, manufacturers either: (a) provide gage housings that incorporate a male fitting 10, as shown in FIGS. 1A and 1B, whereby they must forgo the marketplace in countries that do not allow female luer lock quick-connect fittings and wherein these companies risk the above-described safety issues, or (b) provide gage housings that incorporate female fittings 50, as shown in FIG. 2. Doing the latter, manufacturers avoid the safety problem associated with the male fittings 10 of FIGS. 1A and 1B, but the resulting gage is incompatible with the female luer locks present on existing gage housings that are designed to accept the male fitting. Manufaturers could do both (a) and (b) options, but this is not optimal from either a economic or marketing standpoint.

Thus, there is a need for a device that can provide interchangeable connections between a blood pressure measurement cuff and gage housings that may include other male or female fittings, yet which does not encounter safety issues and is not unduly complex to design, to produce or to use in practice.

SUMMARY OF THE INVENTION

These and other needs are met by a connector for a blood pressure measurement system. The connector comprises a first section that having end (e.g. a barbed-shaped end) adapted to be connected to a cuff, and a second section having a main body. The second section of the connector further includes: (a) a first element that protrudes from the main body, the first element having a threaded outer periphery configured to engage a female fitting, and (b) a second element protruding from the main body and having an outer periphery configured to engage a male fitting. The connector can be made from various suitable materials, such as a plastic material, which, by way of example, can be a thermoplastic material (e.g., a polycarbonate resin). Alternatively, the connector can be constricted from metal or other suitable material.

According to one version, the first section of the connector includes a main body section having a uniform or non-uniform diameter. The main body of the second section of the connector includes a first subsection and a second subsection, wherein the length of the first subsection is greater than the length of the second subsection and/or wherein the outer diameter of the first subsection is substantially equal to the outer diameter of the second subsection.

A continuous lumen is defined within the connector spanning the first section and the second section. The continuous lumen can have a uniform or non-uniform inner diameter, which can be shaped, e.g., to accommodate at least a portion of a male fitting. Moreover, the connector includes an intermediary section disposed between the first section and the second section, wherein the continuous lumen also spans the intermediary section. The intermediary section includes a plurality of surface indentations, e.g., to facilitate grasping, maintaining a grip upon, and manipulating the connector via the intermediary section.

In another embodiment, the connector having generally the same features as the first embodiment, further includes a free spinning outer portion. The outer portion rotates freely about the primary axis of the connector, allowing the inner portion of the connector to advance further into a gage housing.

The connector can be incorporated into a blood pressure measurement system so as to provide highly beneficial versatility and interchangeability among system components. To that end, an exemplary blood pressure measurement system can include, as or among its various components, (a) an inflatable sleeve or cuff that is adapted to be wrapped about a limb of a patient, (b) a first gage housing that includes a fitting having a first shape characteristic, (c) a second gage housing that includes a fitting having a second shape characteristic differing from the first shape characteristic of the gage fitting of the first gage housing, and (d) a connector that includes a first section having an end adapted to be connected to the cuff and a second section adapted to be interchangeably connected to the fitting of the first gage housing and the fitting of the second gage housing.

According to one version, the first shape characteristic of the first gage housing, e.g., the fitting of the first gage housing, is a male fitting, and the second shape characteristic of the second gage housing e.g., the fitting of the second gage housing, is a female gage housing, wherein first and second elements protrude from the second section of the connector. The first element includes an outer periphery that is adapted to engage the female fitting of the second gage housing and the second element is defined by an outer periphery that is adapted to engage the male fitting of the first gage housing. The end of the first section can be connected to the cuff.

Thus, due to its design, the connector can be incorporated within a blood pressure measurement system so as to permit the formation of rapid, easy, reliable and interchangeable individual connections between a cuff, the connector and a gage housing having a male fitting and between a cuff, the connector and a gage housing having a female fitting.

Still other aspects, embodiments and advantages are discussed in detail below with regard to the following detailed description as read in conjunction with the accompanying drawings.

BRIEF DESCRIPTION OF THE DRAWINGS

FIG. 1A is a perspective view of a conventional male fitting of a gage housing;

FIG. 1B is a side view, with partial cut away, of the conventional male fitting of FIG. 1A;

FIG. 2 is a side, sectional view of an exemplary female fitting of a gage housing;

FIG. 3A is a perspective view of a first embodiment of a multipurpose connector for interchangeably connecting a cuff to gage housings having either a male fitting or a female fitting;

FIG. 3B is a side view of the multipurpose connector of FIG. 3A;

FIG. 3C is a side view, shown in section, of the multipurpose connector of FIGS. 3A and 3B;

FIG. 5 is a side view, partially sectioned, of a multipurpose connector according to a second embodiment, depicting the multipurpose connector connected to a female fitting.

DETAILED DESCRIPTION

Figure 4A:
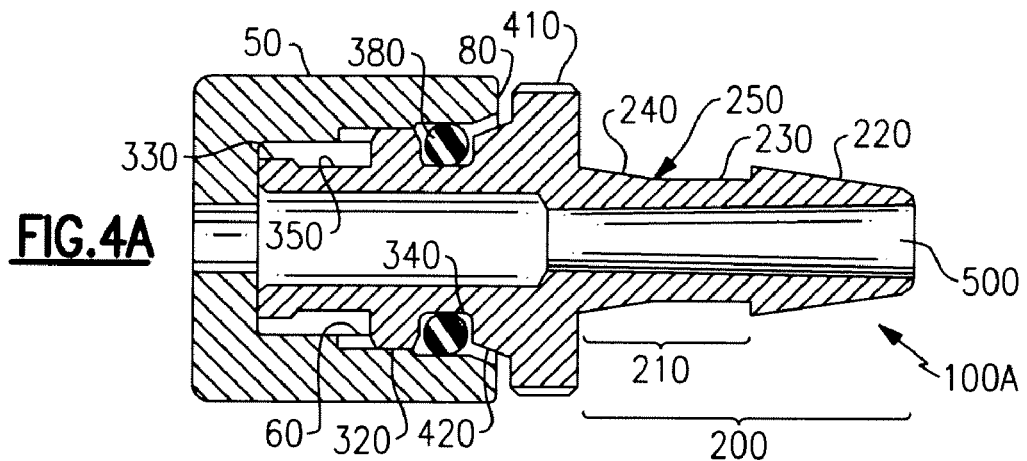
FIGS. 4A-4D are side sectional views of the multipurpose connector of FIGS. 3A-3C, according to various connection scenarios.

Referring to FIGS. 3A-3C, a first embodiment of a multipurpose connector 100 is shown and described herein. The connector 100 is highly advantageous in that due to its design, which is described in detail below, it can be utilized without additional components to interchangeably connect an inflatable blood pressure measurement sleeve or cuff to a wide variety of differently designed gage housings, including gage housings that are equipped with either a male fitting (e.g., the male fitting 10 of the type depicted in FIGS. 1A and 1B) or gage housings that are alternatively equipped with a female fitting (e.g., the female fitting 50 of the type depicted in FIG. 2). As noted previously, current gage housings generally include a female fitting to prevent connection between incompatible devices. For instance, IV lines have female luer locks at the end of an IV line and these luer locks could be easily connected to a male fitting generally used in older blood pressure measuring devices. To prevent the inadvertent connection between an IV line and a male fitting of a gage housing, newer devices are therefore made with a female fitting. Since newer housings typically incorporate a female fitting, the herein described multipurpose connector 100 is necessary to create the fluidic connection between the blood pressure measuring device and the blood pressure cuff. Therefore, the herein described connector advantageously provides connectability between blood pressure cuffs and measuring devices having either a male fitting, generally of an older measuring device, or a female fitting, generally of newer measuring devices. Therefore, the connector 100 provides a beneficial combination of versatility and safety.

The multipurpose connector 100 of FIGS. 3A-3C includes a first section 200 shaped for connection to a cuff disposed at one end of the connector, a second section 300 shaped for connection to a fitting disposed at an opposite end of the connector relative to the first section, and an intermediary section 400 disposed between the first and second sections. As best shown in FIG. 3C, a continuous lumen 500 is defined within the entirety of the axial length of the connector 100, the lumen spanning each of the first section 200, the second section 300 and the intermediary section 400. The lumen 500 can have a substantially uniform diameter or a non-uniform diameter. In accordance with the present embodiment, the lumen 500 has a non-uniform diameter, including the diameter of the lumen within the second section 300 is greater than that within the first section 200. The lumen 500, from both ends of the connector 100, tapers inwardly along its length toward the intermediary section 400.

The connector 100 according to the present embodiment can be made from various durable, yet lightweight and inexpensive materials, such as, for example, plastic, such as, but not limited to thermoplastic materials, including polycarbonate or acrylic resins. Alternatively, however the connector 100 can also be made, at least partially, of metal or other suitable material.

More particularly, the first section 200 of the multipurpose connector 100 is defined by a body area 210 having a barb 220 at one end. In accordance with the present embodiment depicted in FIGS. 3A-3C, the barb 220 enables the connector 100 to be reversibly attached, connected, or otherwise placed into communication with a cuff, as is generally known in the art (e.g., via hose, tubing, or a coupling).

In accordance with the present embodiment as depicted in FIGS. 3A-3C, the remainder of the body area 210 is defined by a first, substantially uniform diameter portion 230 proximate the barb 220 and a second, non-uniform diametral portion 240 extending axially to the intermediary section 400 from a transition point 250. The body area 210 extends from the proximal end of the barb 220, where the transition point 250 is located between the first, uniform diameter portion 230 and the second, non-uniform diameter portion 240. The second, non-uniform diameter portion 240 is located between the transition point 250 and the intermediary section 400 of the connector 100. As best shown in FIG. 3B and according to this embodiment, the outer diameter of the second, non-uniform diameter portion 240 of the first section 200 of the connector 100 tapers from the intermediary section 400 to the transition point 250, wherein the angle of taper is less than about 30° (e.g., about 15°). The increasing diameter of the second, non-uniform diameter portion 240 of the body area 210 is beneficial in that it helps ensure that a fluid-tight connection can quickly and easily occur and reliably be maintained between a cuff and the first section 200 of the connector 100.

The intermediary section 400 of the multipurpose connector 100 includes a first area 410 adjoining the second, non-uniform portion 240 of the first section 200 of the connector and a second area 420 between the first area 410 and the second section 300 of the connector. According to an exemplary embodiment depicted in FIGS. 3A-3C (see, in particular, FIGS. 3A and 3B), the area member 410 includes a plurality of exterior surface indentations 430 so as to facilitate one's ability to grasp, maintain a grip upon, and manipulate (e.g., by hand or with a tool) the first area 410. In addition, the outer diameter of the first area 410 generally is greater than (e.g., at least about 20 percent greater than) that of any other portion of the connector 100. In further accordance with an exemplary embodiment depicted in FIGS. 3A-3C (see, in particular, FIGS. 3B and 3C), the second area 420 has a substantially conical shape and a non-uniform outer diameter, wherein the outer diameter tapers from the first member 410 to the second section 300 of the connector, and the angle of taper is less than about 45° (e.g., about 25°).

The second section 300 of the connector 100 includes a body area 310 from which the first portion 320 and second portion 330 protrude to define a first body subsection 340 (between the first protruding portion 320 and the second area 420 of the intermediary section 400) and a second body subsection 350 (between the first protruding portion 320 and the second protruding portion 330). Generally, the outer periphery of each of the first protruding portion 320 and the second protruding portion 330 is threaded, as further discussed below. Further, the first body subsection 340 is defined such that a sealing member or element, such as an O-ring, can be disposed around the first body subsection 340 to create a fluid-tight connection between the fitting and the connector 100. The sealing member can be integral with the connector, integral with a gage housing, or a separate element disposed around the connector or within a housing.

The outer diameter of the first body subsection 340 and the outer diameter of the second body subsection 350 can be different, or, according to the present embodiment depicted in FIGS. 3A-3C (see, in particular, FIGS. 3B and 3C), can be substantially identical. Moreover, the length of the first body subsection 340 (i.e., the gap between the first protruding portion 320 and the second area 420 of the intermediary section 400) can be equal to, less than, or, according to the present embodiment depicted in FIGS. 3A-3C (see, in particular, FIGS. 3B and 3C), greater than the length of the second body subsection 350 (i.e., the gap between the second protruding portion 330 and the first protruding portion 320). According to this embodiment, a sealing member or element (e.g., O-ring 380, see FIG. 4A) is disposed around the first body subsection 340 so as to provide further assurance that the connection between a gage housing and the second section 300 of the connector 100 is fluid-tight.

The presence of the first protruding portion 320 of the second section 300 enables the connector 100 to connect to a female fitting 50, FIG. 2. Such a connection is shown in FIG. 4A. The presence of the second protruding portion 330 enables the connector 100 to non-simultaneously connect to a male fitting 10, FIGS. 1A and 1B. To that end, no additional parts, devices or adapters are required to be used in order to form either of these connections, thus providing an economic benefit and facilitating the connection process. Thus, the multipurpose connector 100 is quite versatile, such that it can connect either to a female fitting or a male fitting, such as those fittings shown in FIGS. 1A, 1B, and 4A-D.

In furtherance of forming a suitable connection between the connector 100 and a mail fitting 10 (FIGS. 1A and 1B) of a gage housing, the connector 100 is grasped by hand or with a tool (e.g., at the first area 410 of the intermediary section 400), and the male element 40 of the male fitting 10 is inserted into the lumen 500 from the end of the second section 300. The connector 100 (e.g., at the first area 410 of the intermediary section 400) is then twisted clockwise so as to enable the threaded outer periphery of the second protruding portion 330 to "catch" the compatible internal luer thread 30 of the male fitting 10, after which the male element 40 of the male fitting 10 is caused to be sufficiently advanced in the continuous lumen 500 so as to provide a fluid-tight connection between the connector 100 and the gage housing.

Due to the design of the connector, the male fitting 10 can be quickly and easily connected to the connector 100 via the second protruding portion 330. Once this connection occurs and the shaped end 220 of the connector 100 is connected to a cuff, the connector provides a reliable, fluid-tight connection between the cuff and a gage housing to which the male fitting 10 is attached or connected. Exemplary gages that include a male fitting 10 of the type shown in FIGS. 1A and 1B include, but are not limited to, hand aneroid gages, such as the hand aneroid gages commercially available under the "Tycos®" name and product line from Welch Allyn, Inc. of Skaneateles Falls, N.Y.

Moreover, the same connector 100 that can be utilized to connect a male fitting 10 (FIGS. 1A and 1B) to a cuff also can be used to non-simultaneously connect the cuff to a gage housing that includes a female fitting 50, FIG. 2. This dual compatibility is necessary in that newer measurement devices generally include female housings to prevent an inadvertent connection between incompatible devices, such as an IV line and a blood pressure measuring device, for the above-stated reasons. To that end, and in accordance with the exemplary embodiment shown in FIGS. 3A-3C (see, in particular, FIG. 3A), the outer periphery of the first protruding portion 320 is threaded so as to be compatible with the internal thread of a female fitting 50, FIG. 2. Thus, to effect a connection between the connector 100 and the female fitting 50, the multipurpose connector 100 is grasped (e.g., at the first member 410 of the intermediary section 400) and the second protruding portion 330 and the second body subsection 350 are inserted within the female fitting 50. The connector (e.g., at the first member 410 of the intermediary section 400) is then twisted in a clockwise direction so as to enable the threaded outer periphery of the first protruding portion 320 to "catch" the internal threads 60 of the female fitting 50. The connector 100 can then be threadedly advanced into the female fitting 50 until the outer rim 80 of the female fitting is flush with a first side 440 of the first member 410 of the intermediary section 400, thereby providing a fluid-tight connection between the connector 100 and the gage housing. An exemplary gage that includes a female fitting 50, FIG. 2, includes the family of aneroid gages commercially available that incorporate the so-called "Durashock" technology (e.g., the DuraShock Classic) from Welch Allyn, Inc. of Skaneateles Falls, N.Y., such as those described, for example, in U.S. Pat. Nos. 6,615, 666, 6,578,428, 6,481,291 and 6,422,086, the entire contents of which are herein incorporated by reference.

FIGS. 4A-4D depict the multipurpose connector 100 in various exemplary connection scenarios. For purposes of this discussion, the connectors 100A, 100B, 100C and 100D depicted in FIGS. 4A-4D, respectively, each include first and second sections 200, 300 as well as an intermediary section 400. These connectors illustrate typical design variations in the design of the intermediate section 400, wherein the function of the connectors, as described above, is still realized. In FIG. 4A, the connector 100A is connected to a gage housing that includes a female fitting 50, akin to that depicted in FIG. 2. For purposes of this discussion, only the fitting 50 is represented. As shown in FIG. 4A, and if desired, a sealing element (e.g., an O-ring 380) can be disposed around the first body subsection 340 of the connector 100A so as to ensure that the connection between the connector 100 and the female fitting 50 is fluid-tight. Further, the female fitting 50 and the connector 100A have a radial seal connection. The use of the O-ring 380 provides a suitable fluid-tight connection between the two elements.

Figure 4B:
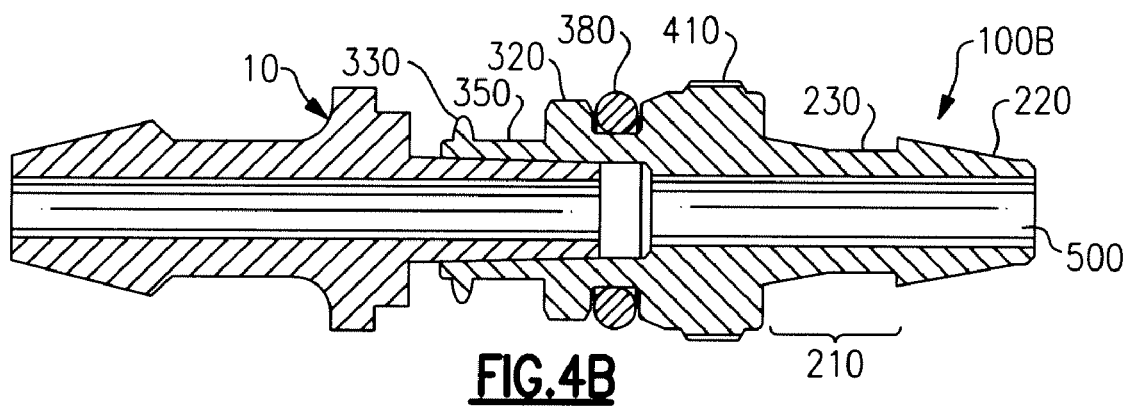
Figure 4C:
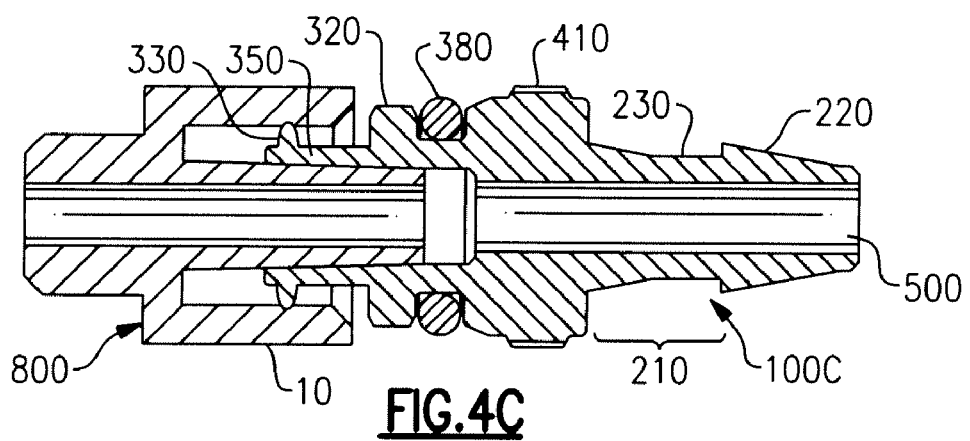

In FIG. 4B, the scenario illustrates a slip-type connection in which the connector 100B has been connected to a slip male fitting 10 of the type shown in FIGS. 1A and 1B, but wherein the male fitting 10 is not part of an attached gage. In that instance, the male fitting 10 is retained within the continuous lumen 500 of the connector 100B via, e.g., a press fit. In FIG. 4C, the connector 100C is shown as connected to a gage housing 800 (only partially shown) that includes a male fitting 10 of the type depicted in FIGS. 1A and 1B. The second protruding portion 330 has a thread that engages the gage housing 800, while the male fitting 10 is retained within the Continuous lumen 500 of the connector 100C.

Figure 4D:
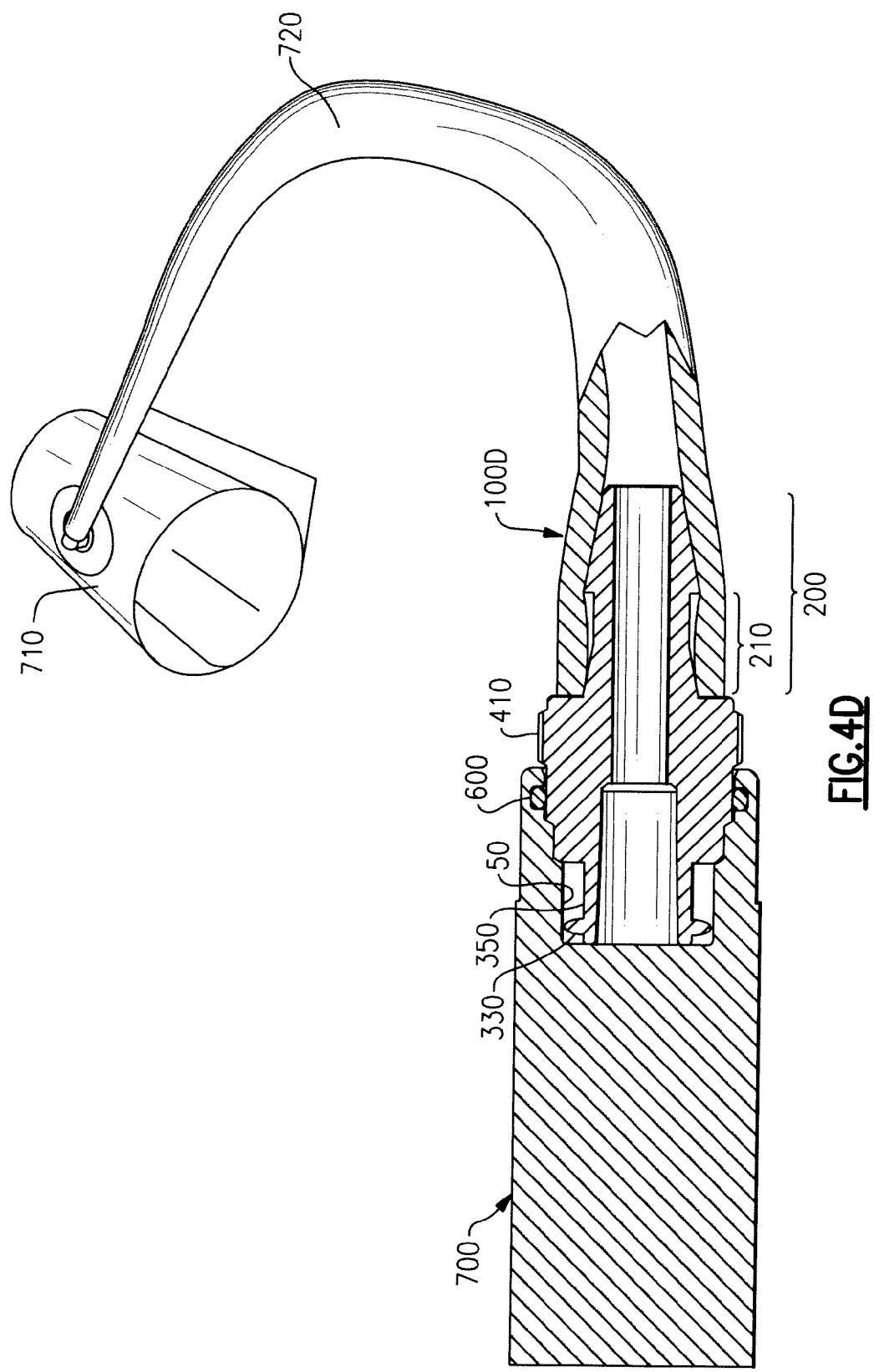

FIG. 4D depicts still another connection scenario for the connector 100D. The gage housing 700 contains a female fining 50 having threading for engaging the connector 100D. Blood pressure cuff 710 engages the barb 220 of the connector 100D via tubing 720. Further, the female fitting 50 contains a sealing element 600, such as an O-ring, to create a fluid-tight connection between the connector 100D and the female fitting 50.

Referring to FIG. 5, there is shown a multipurpose connector according to a second embodiment. Similar parts are labeled with the same reference numerals, for the sake of clarity. The connector 150 is similar to the first embodiment, however, the connector 150 also has a free spinning outer portion 450. The connector 150 includes a first section 200 with a shaped end 220 and a body area 210. The connector further includes an inner body 455 that is substantially cylindrical, and defined within the inner body 455 is a continuous lumen 500 that, according to this embodiment, is non-uniform. The first section 200 and the intermediary section 400 defines the continuous lumen 500 that tapers from the first section 200 to the intermediary section 400. The second section 300 defines a lumen 500 tapering from the second section 300 toward the intermediary section 400. While the lumen 500 is continuous, it has two different sizes (i.e., diameters) for engaging different elements (i.e., the second section is sized such that it can retain a male fitting such as the one shown in FIGS. 1A and 1B).

The outer portion 450 rotates freely about the primary axis 151 of the connector 150. Therefore, the connector 150 creates an axial seal between a female fitting 900 and the connector 150. The axial seal is created by the outer portion 450 being rotated around the inner body 455 and thereby advancing the entire connector 150, and more specifically causing the second protruding portion 330 to squeeze a sealing element 600 (e.g., an O-ring) between the female fitting 900 and the connector 150. The sealing element 600 assists in providing a fluid-tight connection between the female fitting 900 and the connector 150. Moreover, FIG. 5 illustrates a tube-to-tube connection wherein the connector 150 has been connected (e.g., threadedly connected) to the female fitting 900 of aneroid gage (partially shown), the fitting including a barbed end 950 for attachment to tubing (not shown).

Thus, FIGS. 4A-4D and 5 illustrate the beneficial versatility that is obtained through use of the connector 100A, 100B, 100C, 100D, 150—that is, the multipurpose connector 100A, 100B, 100C, 100D, 150 can be interchangeably individually connected to various gages or gage housings regardless of whether the particular gage includes a male fitting 10, FIGS. 1A and 1B or a female fitting 50, FIG. 2. These benefits allow those who use the connector 100 to continue to confidently and economically employ the widest array of both existing and newly manufactured gages.

Moreover, in view of such versatility, a system can be provided that includes at least one multipurpose connector 100, 150 and a plurality of other pieces of equipment or devices for obtaining a blood pressure measurement. Such a system can include at least one connector 100, 150, as described herein and depicted in FIGS. 3A-3C and 5, respectively, and a plurality of gages or gage housings, at least one of which is equipped with a male fitting (e.g., as shown in FIG. 4C), and at least another of which is equipped a female fitting (e.g., as shown in FIG. 4A), and can still further include one or more blood pressure measurement sleeves or cuffs. The one or more cuffs can be, for example, of the type denoted by reference numeral 1000 in FIGS. 29, 33 and 34 of co-pending and commonly owned U.S. patent application Ser. No. 11/230,117, the entirety of which is incorporated by reference herein. Thus, the one or more cuffs can be of the same or varied size (e.g., infant size, pediatric size, small adult size, adult size and large adult size), wherein the cuff size can be denoted, e.g., by textual and/or pictorial indicia on the cuff, and wherein the cuff can be dimensioned to fit either the arm or the thigh of the patient, and wherein the one or more cuffs can be durable or disposable. By disposable, it is meant that the cuff can be made for either single use or single patient use.

By employing such a system, one can quickly, easily and reliably obtain a connection, via the herein described connector, between a cuff and a gage housing regardless of whether the gage housing includes a male fitting or a female fitting. Such a system is interchangeable in that one also can quickly, easily and reliably switch from a connection between a cuff, a connector 100, 150, and a gage housing that includes a male fitting to a connection between a cuff, the same or different connector 100, 150, and a gage housing that includes a female fitting, or vice versa.

PARTS LIST FOR FIGS. 1A-5

10 male fitting
20 open connection end, male fitting
30 internal luer thread, male fitting
40 male connection element, male fitting
50 female fitting
60 internal threading, female fitting
70 internal width, female fitting 80 outer rim, female fitting
100 connector, first embodiment
100A connector
100B connector
100C connector
100D connector
150 connector, second embodiment
151 primary axis, connector
200 first section of connector
210 body area, first section
220 barb or shaped end
230 first, uniform diameter portion of body area, first section
240 second, non-uniform diameter portion of body area, first section
250 transition point
300 second section
310 body area of second section
320 first protruding portion, second section
330 second protruding portion, second section
340 first body subsection, second section
350 second body subsection second section
380 O-ring
400 intermediary section
410 first area, intermediary section
420 second area, intermediary section
430 surface indentations
440 first side of first member of intermediary section
450 free spinning outer portion
455 inner body
500 continuous lumen
600 sealing element
700 gage housing
800 gage housing
900 gage housing
950 hose/tubing Although various embodiments have been described herein with reference to details of certain embodiments, it is not intended that such details be regarded as limiting the scope of coverage, except as and to the extent such embodiment(s) are included in the following claims. That is, the foregoing description is merely illustrative, and it should be understood that variations and modifications can be effected without departing from the scope of the embodiments set forth in the following claims. Moreover, any document(s) mentioned herein are incorporated by reference in their entirety, as are any other documents that are referenced within the document(s) mentioned herein.

We claim:

1. A sphygmomanometer system that enables a plurality of blood pressure measurements to be interchangeably performed, said system comprising:
    an inflatable cuff adapted to be wrapped about a limb of a patient;
    a first gage housing including a male luer lock having a wall that at least partly surrounds a male element, said wall containing thread on an internal surface;
    a second gage housing including a female filling with a wall defining a tubular opening; and
    a dually compatible connector comprising:
        a first end connected to the cuff; and
        a second end adapted to be interchangeably connected to said male luer lock and said female fitting, thereby enabling use of the cuff in cooperation with either said first or said second gage housing.

2. The system of claim 1, wherein a first element and a second coaxial element protrude from the second end of said connector, said first element having an outer periphery adapted to engage said female fitting, and said second element having a threaded outer periphery adapted to threadedly engage the internal wall surface of said male luer lock.

3. The system of claim 1, wherein said connector further comprises:
    a continuous lumen defined within said connector and spanning said first end and said second end, wherein said continuous lumen has an inner diameter.

4. The system of claim 3, wherein the continuous lumen is sized and shaped to accommodate and form a fluid tight seal against at least a portion of said male element of said male luer lock.

5. The system of claim 3, wherein the inner diameter of the continuous lumen is non-uniform.

6. The system of claim 1, wherein said connector further comprises:
    an intermediary section between said first end and said second end, having an effective outer diameter greater than that of said first end and that of said second end.

7. The system of claim 1, wherein said first end of said connector is barbed.

8. The system of claim 2, wherein said first element also has a threaded outer periphery and is adapted to threadedly engage said female fitting of said second gage housing.

9. The system of claim 2, wherein said first element and said second element, both of said connector, differ from each other in diameter.

10. The system of claim 1, wherein said connector is configured to be releasably connected to said female fitting by a technique selected from the group consisting of: (a) snap fitting, (b) threaded connection, (c) friction fitting, (d) luer, and (e) a combination of at least two of (a), (b), (c), and (d).

11. The system of claim 1, wherein said female fitting and connector are coupled by a technique selected from the group consisting of: (a) a luer taper, (b) an axial seal, and (c) a radial seal.

12. The system of claim 1, further comprising a sealing element around said second end of said connector to facilitate a fluid-tight seal against either said first or second gage housing.

13. The system of claim 12 wherein said sealing element comprises an O-ring.

14. The system of claim 1, wherein said connector further comprises an outer portion around said second end.

15. The system of claim 14, wherein said outer portion rotates around said second end to facilitate the formation of a fluid-tight sealing against either said first or second gage housing.

* * * * *